| United States Patent [19] | [11] Patent Number: 4,859,078 |
| Bowman et al. | [45] Date of Patent: Aug. 22, 1989 |

[54] APPARATUS FOR THE NON-INVASIVE MEASUREMENT OF THERMAL PROPERTIES AND PERFUSION RATES OF BIOMATERIALS

[75] Inventors: Harry F. Bowman, Needham; James C. Weaver, Sudbury, both of Mass.

[73] Assignee: Massachusetts Institute of Technology, Cambridge, Mass.

[21] Appl. No.: 195,336

[22] Filed: May 18, 1988

Related U.S. Application Data

[63] Continuation of Ser. No. 828,001, Feb. 7, 1986, abandoned, which is a continuation-in-part of Ser. No. 701,434, Feb. 11, 1985, abandoned, which is a continuation of Ser. No. 421,533, Sep. 22, 1982, abandoned.

[51] Int. Cl.$^4$ .................... G01N 25/18; G01K 17/08; A61B 5/02
[52] U.S. Cl. ........................ 374/44; 374/43; 374/29; 128/691; 128/736
[58] Field of Search ............ 374/29, 30, 43, 44; 128/691, 694, 713, 736

[56] References Cited

U.S. PATENT DOCUMENTS

| 3,238,775 | 3/1966 | Watts | 374/30 |
| 3,256,734 | 6/1966 | Storke, Jr. | 374/29 |
| 3,367,182 | 2/1968 | Baxter | 374/29 |
| 3,605,490 | 9/1971 | Progelhof et al. | 374/29 |
| 3,605,494 | 9/1971 | Progelhof et al. | 374/29 |
| 3,720,103 | 3/1973 | Adams et al. | 374/29 |
| 3,877,463 | 4/1975 | Cary et al. | 374/43 |
| 3,971,246 | 7/1976 | Sumikama et al. | 374/44 |
| 4,059,982 | 11/1977 | Bowman | 374/44 |
| 4,125,012 | 11/1978 | Madsen | 374/45 |

FOREIGN PATENT DOCUMENTS

| 2724846 | 12/1978 | Fed. Rep. of Germany | 374/43 |
| 0450972 | 11/1974 | U.S.S.R. | 374/29 |
| 0911277 | 3/1982 | U.S.S.R. | 374/44 |

*Primary Examiner*—William A. Cuchlinski, Jr.
*Assistant Examiner*—Thomas B. Will
*Attorney, Agent, or Firm*—Paul J. Cook

[57] ABSTRACT

Thermal conductivity, thermal diffusivity and/or fluid perfusion within a medium such as cutaneous tissue is non-invasively measured by at least two heating and temperature sensor. One sensor is positioned in thermal communication with the medium and a second sensor is positioned thermal communication with the first sensor. Both sensor are heated (or cooled) so as to substantially prevent net heat flow between them. In this manner, net heat flow between the first sensor and the medium can be measured, which measurements allow determination of the thermal conductivity, thermal diffusivity and/or fluid perfusion within the medium.

15 Claims, 4 Drawing Sheets point of departure from linearity due to change in value of $\omega$ from 0 to $\omega \neq 0$

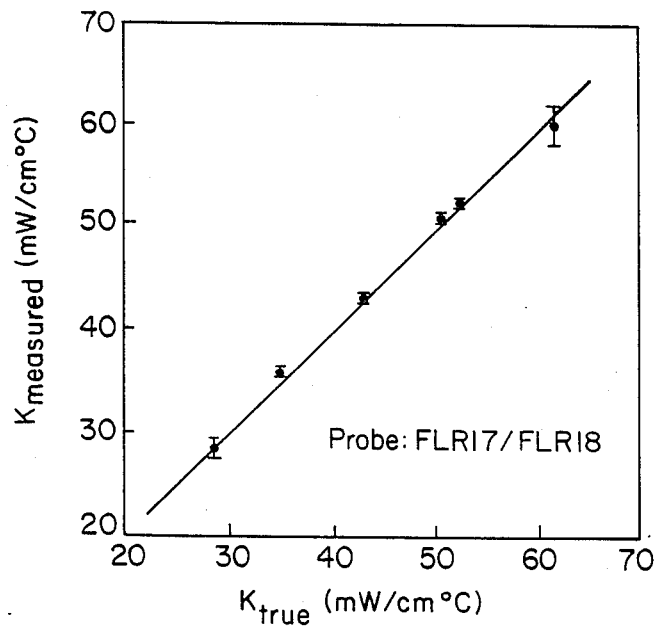
Fig. 6 Measured thermal conductivity versus true thermal conductivity. The average measurement is 1.4%.
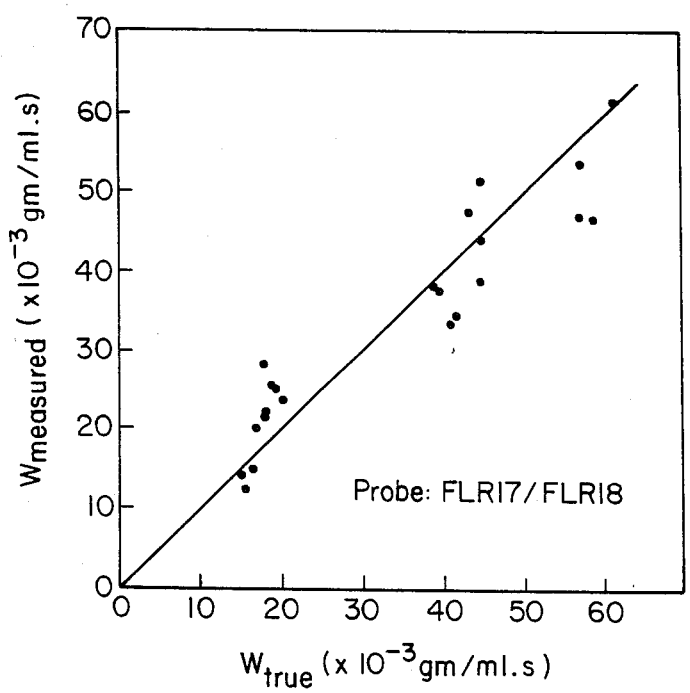
Fig. 7 Perfusion calculated from power requirement versus true perfusion. Average measurement error is 16.9%

APPARATUS FOR THE NON-INVASIVE MEASUREMENT OF THERMAL PROPERTIES AND PERFUSION RATES OF BIOMATERIALS

This is a continuation of copending application Ser. No. 828,001 filed on 2/7/86, now abandoned, which is a continuation of 701,434, now abandoned, which is a continuation of Ser. No. 421,533, filed 9/22/82, now abandoned.

BACKGROUND OF THE INVENTION

A knowledge of the thermal properties of biomaterials has long been considered important to researchers and others interested in increasing man's understanding of the nature of materials and their thermal interactions, as well as to designers of equipment and systems in which the thermal characteristics of the materials used therein or operated thereon are of significance. For example, important information concerning biological materials, such as human and animal tissues, can be obtained from knowledge of the thermal properties thereof.

Thus, it is known that biomaterials are capable of heat transfers by virtue of a temperature gradient, such heat transfer capability being especially important in living biomaterials because the state of life thereof, for example, may depend on the maintenance of a specific temperature level. Heat transfer by conduction is usually most important in determining the heat transfer within the biological medium and such heat transfer is best characterized in the steady-state by the thermal conductivity, $K$, of the medium and in the non-steady state of its thermal diffusivity, $\alpha$. Since there is no presently known method of determining $K$ and $\alpha$ of a biomaterial from a knowledge of some other fundamental property or properties thereof, it is necessary to devise appropriate processes and apparatus to measure $K$ and $\alpha$ in some appropriate manner. Accordingly, there has been an increasing utilization, particularly in medical research and clinical laboratories, of processes which require heat transfer through biological materials, such as in cryobiology (e.g., cyrosurgery), in tissue and organ preservation, and in frostbite studies, for example. Other procedures which are heat transfer dependent and, thus, require a knowledge of thermal properties include clinical applications of heated gases or liquids, ultrasonic wave energy, microwave energy and laser beam energy in both diagnostic and therapeutic operating modes - examples being laser surgery and hyperthermia thermal therapy, as an emerging modality for the treatment of cancer.

Such processes require more extensive and more reliable information concerning the thermophysical properties of such materials and, in particular, information concerning the thermal conductivities and thermal diffusivities thereof which permit the determination of temperature distributions, heat transfer rates and, in turn, the flow rates of fluids through the biological medium. Perfusion, the volume flow rate of blood per unit mass or volume of tissue is a primary factor in the local transport of heat, oxygen, drugs and nutrients - thus in the maintenance, assessment and medical intervention of life processes. It is particularly important, for example, to monitor the flow rate of blood through tissue so that flow disturbances can be monitored and corrective action taken in cases where maldistribution of blood flow in a patient would have unfavorable and possible fatal consequences. For example, it would be desirable to provide information during open heart surgery as to blood perfusion rates in the myocardium to assess the success of revascularization procedures and the existence of small vessel disease so that subsequent incisions are not required after primary arterial blood flow correction. Furthermore, with some patients, it is necessary to determine whether further medical assistance to the patient is required. In addition, such information is essential in treating patients afflicted with ulcerated extremities and in the most efficacious application of transcutaneous gas measurements.

Techniques which have been applied to the measurement of thermal properties of biological materials have included both invasive and non-invasive techniques. A general summary of such techniques and the limitations thereof is presented in the text, *Annual Review of Biophysics and Bioengineering,* "Theory Measurement and Application of Thermal Properties of Biomaterials," H. Frederick Bowman et al, pp. 43-80, Vol. 4, 1975. A review of the most promising thermal techniques (invasive and non-invasive) in the measurement of perfusion is presented in the text, Heat Transfer in Medicine and Biology, Vol. 2, "Estimation of Tissue Blood Flow," Chapter 9, H. Frederick Bowman, Plenum Publishing Corporation, 1984.

Knowledge of perfusion is generally known to be of importance in the clinical evaluation of patients, in selecting therapeutic interventions and in general patient management. Altough measurement of perfusion in deep tissue, that located greater than about 0.5 cm from the tissue surface, generally requires invasive procedures and devices (Bowman Patent No. 4,059,982; Bowman, ibid, and general literature reviews), several important clinical and research problems require the accurate measurement in the outer layer of tissue surface. Examplary problems are the measurement of: epicardial perfusion following open heart surgery, rate of revascularization of burn patients, requirement of and/or location of where to amputate ulcerated extremities. Sitll another important problem is the measurement of skin perfusion during transcutaneous blood gas monitoring, wherein it would be desirable to determine non-invasively both perfusion and the temperature of the blood in the capillaries which are located within about 100 to 300 microns of the skin surface, without which the transcutaneous measurements are inaccurate, such that present devices and methodology are generally not capable of providing transcutaneous measurements on adults. In general, therefore, it is important to have non-invasive means for accurate measurement of tissue perfusion in the layer of tissue located within the first several millimeters of the tissue surface.

While prior non-invasive techniques can provide some information about surface region perfusion, they have been limited in that the information obtained is generally qualitative and inaccurate, since the thermal coupling between the measuring device and the system being measured is not accounted for and since means for thermally guarding or actively shielding the surface sensor are not provided, with the consequence thereof being that the quantitative methodology exemplified in the use of the thermal diffusion probe (Bowman, U.S. Pat. No. 4,059,982; and reviews entitled "Theory, Measurement and Application of Thermal Properties of Biomaterials" and "Estimation of Tissue Blood Flow," as aforementioned), cannot be used. Thus, generally speaking, accurate measurement of perfusion has been limited to invasive means, during which the sensor(s) are surrounded completely by and fully exposed to the influence of the very medium, the tissue or biomaterial, for which the perfusion measurement is sought. Such invasive techniques involve the implantation within the specimen material of heat sources (or sinks) which may also serve as temperature sensors. Probes which have been utilized for this purpose include the thermal comparator, the heated thermocouple and the heated thermistor. However, invasive probes are undersirable since they cause discomfort, trauma to the patient and danger of infection.

Accordingly, it would be highly desirable to provide a non-invasive means for measuring blood perfusion in order to reduce patient trauma and risk of infection while providing an accurate means of blood perfusion through characterizing the influence of the measurement device, while avoiding the deleterious influences of the ambient thermal environment, in order to reduce patient trauma and discomfort while providing an accurate means for measuring blood perfusion in the surface layer of tissue.

SUMMARY OF THE INVENTION

In accordance with this invention, thermal properties and perfusion of tissue near the surface are measured non-invasively by determining the rate of heat transfers from one or more elements, exemplified by thermistors, from a composite device into and through the surface tissue layer in a manner which prevents heat transfer, or causes heat transfer to occur at a calculable rate, from at least one element of the composite device, to the ambient environment adjacent the surface tissue. The rate of heat transfer from at least one element then can be used to determine the amount of perfusion in the contacting surface tissue. For example, one surface of a first thermistor flake is placed in direct contact with the skin. The second surface of the first thermistor flake is contacted by an intervening thin thermal insulator to a second thermistor flake. Electrical power is supplied to the first thermistor thereby to heat it while the temperature of the first thermistor is monitored. The second thermistor acts as an active, regulated thermal shield or thermal guard to prevent heat from flowing from the first thermistor into the ambient environment adjacent the tissue surface. Therefore, electrical power is supplied to the second thermistor in order to maintain the temperature of the second thermistor at the same temperature as the first thermistor. When the temperatures of both thermistors are maintained at the same value, there exists an essentially adiabatic surface between the two thermistor flakes and heat transfer can only occur from the first thermistor into the surface tissue with which it is in contact The electrical power needed to maintain the first thermistor at a predetermined temperature then is monitored and is related directly to the rate of heat transfer from the first thermistor to the contacting surface layer. This power requirement of the first thermistor than can be related to the uptake of heat by the subsurface flowing blood and this measurement can be directly related to thermal conductivity, thermal diffusivity and/or blood perfusion within the surface layer. In order to provide accurate measurements of thermal conductivity and thermal diffusivity and therefore perfusion, it is necessary that the apparatus of the invention have a small thermal time constant so that there is little or no time lag between thermal measurement and responsive heating or cooling of the first thermistor.

BRIEF DESCRIPTION OF THE DRAWINGS

FIG. 6 shows the accuracy of thermal conductivity measurement over range relevant to most physiological applications.

FIG. 7 shows sensitivity of the invention to known changes in perfusion in isolated rat liver in which total blood flow was varied and proportional distribution was determined using microsperes.

DESCRIPTION OF SPECIFIC EMBODIMENTS

Figure 1:
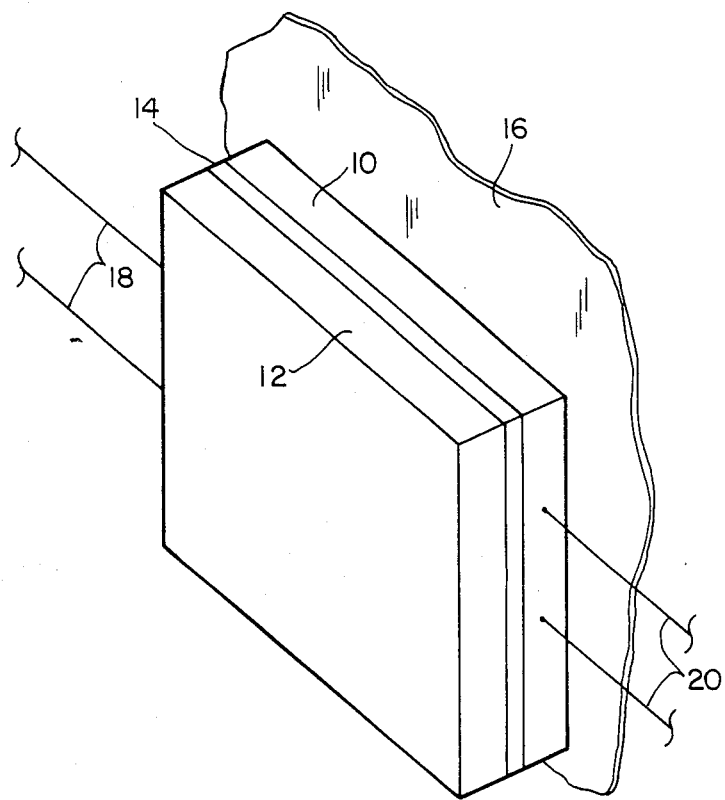
FIG. 1 is an isometric view representative of the apparatus of this invention positioned adjacent to a cutaneous layer.

In accordance with this invention, thermal conductivity, thermal diffusivity, fluid perfusion are measured in e.g. body tissues such as the cutaneous layer, and directed to the subcutaneous flowing fluid, e.g. blood. In order to precisely measure this heat transfer, it is preferred that heat transfer from the distal surface of the heating (or cooling) and temperature sensing means to the surrounding atmosphere or environment be substantially prevented. Otherwise, there would exist bidirectional heat transfer from the source of heat which, unless differentiated, will result in erroneous measurement of heat transfers through the surface layer, thereby resulting in erroneous measurement of thermal properties and blood perfusion. Power is supplied to the heating (or cooling) and temperature sensing means sufficient to maintain the source of heat at a constant temperature. By operating in this manner, there is no heat flow from the source of heat (or cooling) to the surrounding atmosphere or environment other than through the cutaneous layer. In order to accomplish this, a second source ("Guard") of heat is provided to supply (or remove) heat to the heating (or cooling) and temperature sensing means so that the net heat flow from the distal surface is substantially zero. The second source (Guard) of heat is either utilized alone or in combination with insulating means to insulate the heating (or cooling) and temperature sensing means from the outside atmosphere or environment, thereby providing additional isolation of heat transfer through the cutaneous layer. The overall thermal time response of the apparatus of this invention is sufficiently small that there is little or no time lag, typically less than about 5 sec, preferably less than about 1 sec, between the temperature measurement by the temperature sensing means and provision of power to the apparatus to maintain the source of heat at a constant temperature. This rapid response to heat flow, i.e., response time of less than about 5 sec, preferably less than about 1 sec, allows more accurate means of measuring perfusion. The thermal time response is regulated by decreasing the size and mass of the apparatus and utilizing elements of the apparatus with high thermal conductivity.

In an alternative embodiment of the invention, means can be provided to measure the heat flow from the first heating and sensing means (in contact with the surface of the cutaneous layer) to the second heating and sensing means. By knowing the heat produced by the first heating and sensing means, the net rate of heat flow into the cutaneous layer can be determined and related to thermal conductivity, thermal diffusivity and/or fluid perfusion with the medium. For the reasons set forth above, this apparatus also must have a short thermal characteristic time. Suitable heating and temperature sensing means includes thermistor, thermocouples, peltier junctions, semiconductor junction devices and similar devices. Heat produced by the heating and temperature sensing means is related to the power supplied to the means in a manner well known in the art. The rate of heat transfer through the surface layer is related to blood perfusion in accordance with the following mathematical relationships.

Mathematical Model

1. Tissue layer 1 (Surface Tissue)

$$k_1 \nabla^2 T_1 + qmet_1 - \omega_1 Cb_1(T_1 - T_a) = \rho_1 C_1 \frac{\partial T_1}{\partial t} \quad \text{Equation 1}$$

2. Tissue medium 2 (Underlying Tissue)

$$K_2 \nabla^2 T_2 + qmet_2 - \omega_2 Cb_2(T_2 - T_a) = \rho_2 C_2 \frac{\partial T_2}{\partial t} \quad \text{Equation 2}$$

3. First heating and temperature sensing means is contact communication with surface tissue $$K_3 \nabla^2 T_3 + (\Gamma_3 + \beta_3 f[t]) = \rho_3 C_3 \frac{\partial T_3}{\partial t} \quad \text{Equation 3}$$

4. Second heating and temperature sensing means in contact communication with first heating and sensing means (Guard)

$$K_4 \nabla^2 T_4 + (\Gamma_4 + \beta_4 f[t]) = \rho_4 C_4 \frac{\partial T_4}{\partial t} \quad \text{Equation 4}$$

In the above,
k is thermal conductivity,
$\nabla^2$ is the Laplacian Operator
qmet is metabolic heat generation
w is perfusion
$c_b$ is heat capacity of blood
T is temperature
$T_a$ is temperature of arterial blood
$\rho$ is density
C is heat capacity
T/t is time rate of change of temperature Since the first heating (or cooling) and temperature sensing means communicates with the adjacent medium, e.g. surface tissue, it is essential that the governing differential equations (Equations 1, 2, and 3) be solved in a coupled fashion in conjunction with the appropriate boundary and initial conditions so as to define the thermal phenomena taking place. Using the solution techniques taught in U.S. Pat. No. 4,059,982, which is incorporated herein by reference, thermal conductivity, thermal diffusivity and perfusion can be quantified for a wide range of geometries of the medium and heating and temperature sensing means. When appropriate, (e.g. when a non zero second heat path from the first heating and sensing means is allowed), the second heating and temperature sensing means also needs to be analytically modelled and its temperature field determined by solving Equation 4 with appropriate coupling and boundary conditions. These solutions may utilize cartesian, cylindrical, spherical or other coordinate systems according to the choice of geometry of the first and second heating (cooling) and temperature sensing means, and may be evaluated using either numerical or analytical solution procedures.

Figure 3:
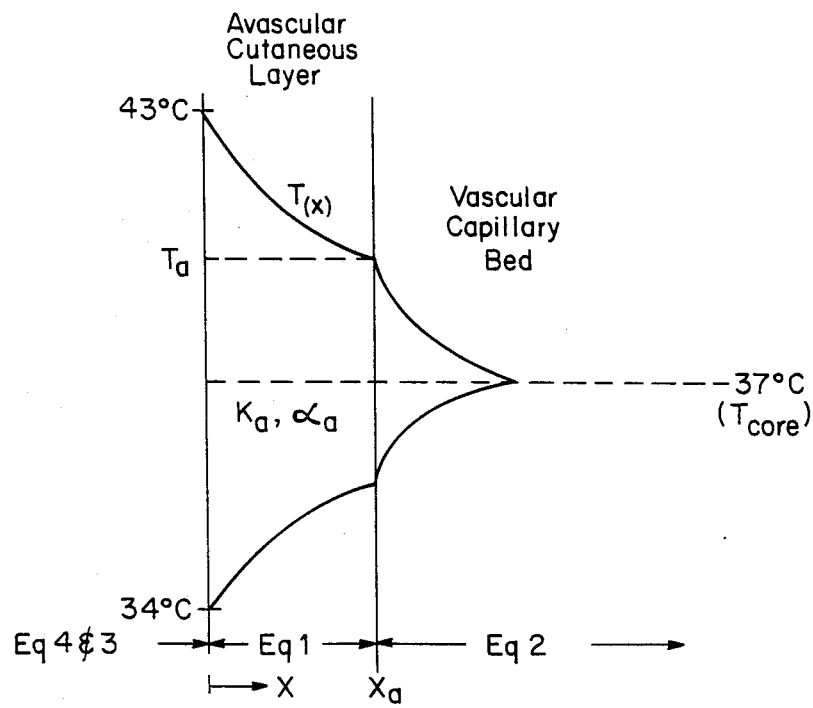
FIG. 3 is a schematic diagram of the device-skin interface with typical temperature profiles, T(x).

Referring to FIG. 3 which indicates the salient features of the apparatus/avascular-cutaneous/capillary bed configuration, the following process is preferred. A first process provides determination of the thickness, $x_a$, of the avascular cutaneous tissue; at a thickness greater than $x_a$, blood perfusion occurs. The apparatus of this invention also can be applied to any site on the body to determine the body core temperature, i.e., the temperature several centimeters away from the cutaneous surface in the direction perpendicular into the body, which temperature constitutes the asymtotic value of the temperature field. Alternatively, any of the following processes may be used to determine core temperature.

1. Rectal Sensor: A temperature sensing means such as a thermistor, thermocouple, etc. is placed rectally in the conventional manner well known in the art. Such placement is body penetrating but not invasive of tissue, and therefore, an accepted safe procedure.

2. Buccal Membrane: A somewhat less desirable process consists of placing a temperature sensing means within the mouth onto the buccal membrane.

3. Zero Heat Flux: As disclosed in U.S. Pat. No. 3,217,538 and Tamura, T., Nemoto, T. and Togawa, T. (1979), "A Zero-Heat-Flow transducer for Monitoring Perfusion Blood Temperature," IEEE Trans. Biomed. Engr., BME-26 644–646.

Figure 4:
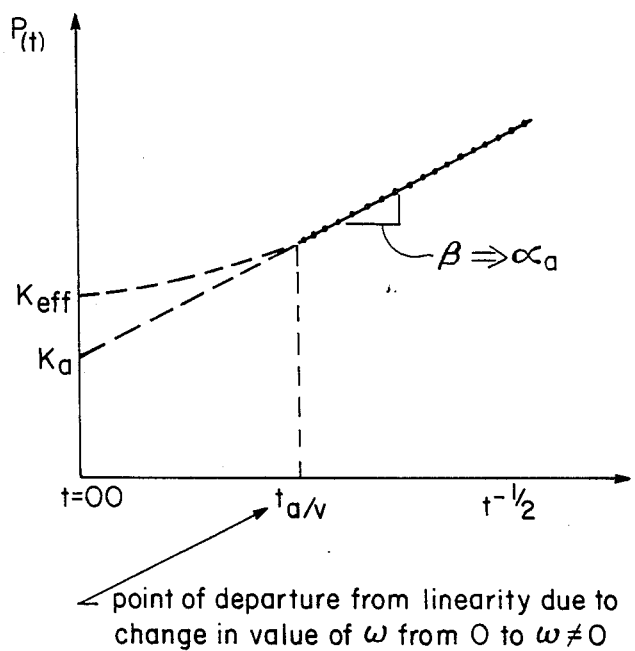
FIG. 4 is a graph of power utilzied in the apparatus of this invention as a function of time to the minus one-half power.

The volume average temperature of the first heating (or cooling) means is then quickly, in stepwise fashion, raised (or lowered) by several degrees. Typically, the time required for this stepwise heating is less than approximately 1 second, preferably less than approximately 0.01 second. Typically, the magnitude of the temperature step is approximately 1 to 10° C., preferable about 4° C. The power, P(t), required to maintain this temperature step is monitored, and compared to the behavior expected for a completely avascular tissue. More specifically still, it is often useful to determine P(t) as function of $t^{-\frac{1}{2}}$, or some other generally non-linear function of the time, f(t), where t is the time from the applicantion of power to impose the temperature step increase (or decrease). As the temperature rise field associated with the stepwise change propagates into the tissue, an analytical relationship is determined wherein P(t) verses f(t) constitutes a straight line as exemplified in FIG. 4.

In the exemplary case, wherein a small (e.g. 50 to 1,000 microns diameter) first heating (or cooling) means is employed, such that the isotherms within the avascular tissue are approximately hemispherical at a distance approxiamtely 50 to 1,000 microns, then the infinite time extrapolation of the straight line response determined at specific times (determined for suitable geometries and sizes) (e.g., 1 to 5 seconds) yields a value for the thermal conductivity, $K_a$, of the avascular tissue, and the slope of the so-determined straight line yields the thermal diffusivity, $\alpha_a$, of the avascular tissue. Further, when the temperature rise field reaches the avascular/capillary boundary, a departure from linearity occurs because of increased ability to remove (add) heat by the mechanism of perfusion. Determination of the time when this departure occurs, in combination with $K_a$ and $\alpha_a$, allows the distance, $x_a$, between the first heating (or cooling) means and the avascular/capillary boundary, to be determined as shown in FIG. 3. Finally, the intercept of P(t) non-linearly extrapolated to infinite time provides a determination of $k_{effective}$, which together with a conventional table value of intrinsic thermal conductivity for a capillary bed, allows determination of the perfusion, $w_{cap}$, in the capillary bed. When additionally desired, the temperature field which is consistent with these determinations can be calculated. For example, a self-consistant, interative computation approach which is well known in the art and the teachings of U.S. Pat. No. 4,059,982 can be used with Equations 1 through 4 where it is assumed in this exemplary case that $w_1$ of equation 1 is equal to zero. Once the temperature field is determined, the temperature at the avascular/capillary bed, $T_a$, can be determined. The overall process of causing the stepwise temperature and the subsequent monitoring and related computations are preferably carried out in real-time using a computer.

At this point in the exemplary process, the following parameters of the cutaneous tissue have been determined:

1. The thermal conductivity of the avascular tissue, $k_a$ (i.e., $K_1$).
2. The thermal diffusivity of the avascular tissue $\alpha_a$ (i.e., $K_1$)
3. The thickness of avascular tissue, $x_a$.
4. The thermal conductivity at steady state, $K_{ss}$ (i.e., $K_{eff}$)
5. The thermal conductivity in the vascular region, $K_{ss}$ (i.e. $K_2$)
6. The outermost capillary bed perfusion, $w_{cap}$.
7. The avascular/capillary boundary temperature, $T_a$.

Referring to FIG. 1, the apparatus of this invention includes a first thermistor 10, adhered to a second thermistor 12 by a flexible electrically insulating adhesive composition 14. The first thermistor 10 is positioned adjacent to and in direct thermal communication with the surface of the tissue medium 16. Power is supplied to thermistor 12 through electrical leads 18 and power is supplied to thermistor 10 through electrical leads 20.

Figure 2:
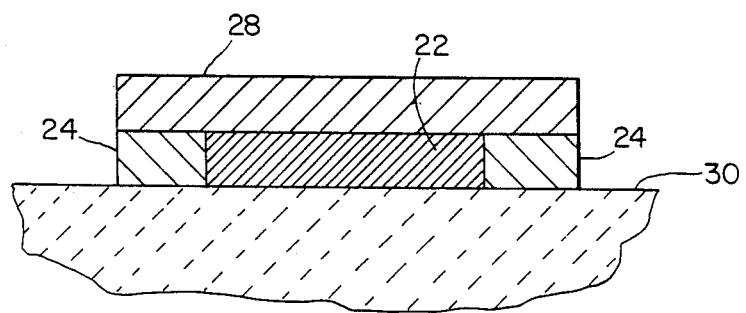
FIG. 2 shows an alternative embodiment representative of this invention.

Referring to FIG. 2, an alternative apparatus of this invention is shown. The first thermistor 22 is positioned in contact with the surface of a medium 30 such as the cutaneous layer. The temperature of thermistor 22 is maintained constant by guard thermistors 24 (annular shaped), and 28 in response to the temperature of thermistor 22. Since the power applied to thermistor 22 is known and its surfaces in contact with thermistors 24 and 28 are essentially adiabatic, the net heat flow from thermistor 22 is directed solely into the cutaneous layer 30. The heat flow rate through the surface of cutaneous layer 30 then is related to thermal conductivity, thermal diffusivity and/or fluid perfusion within cutaneous layer 30. The thermal response time of the apparatus of FIG. 2 is less than about 5 sec., preferably less than about 1 sec.

EXAMPLE I

Figure 5:
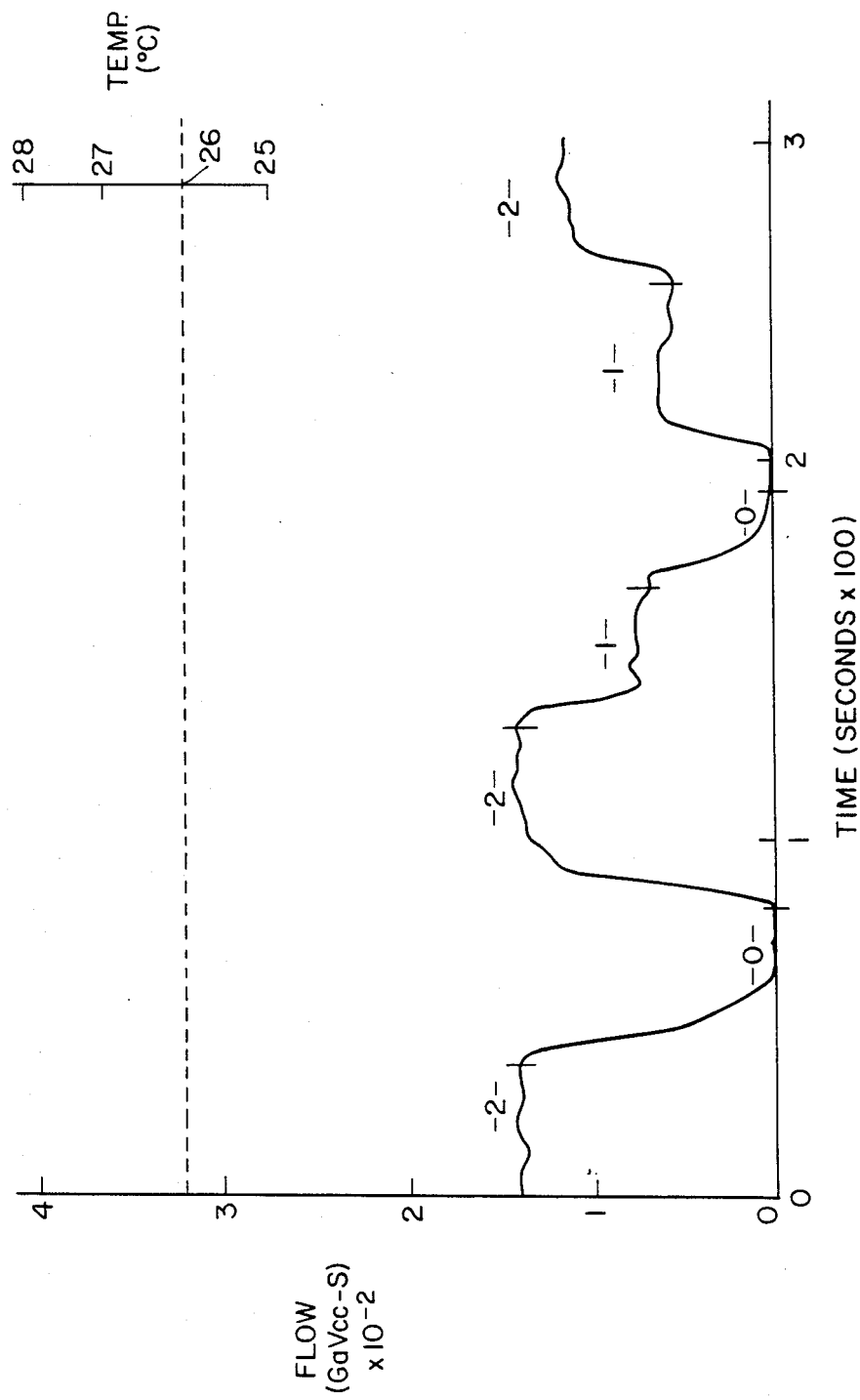
FIG. 5 shows sensitivity of the invention to changes in "flow" induced by electromagnetic stirring of a liquid media.

FIG. 5 shows the sensitivity of the present non-invasive invention using two back-to-back thermistor flakes shown in FIG. 1 in a stirred liquid medium to simulate flow. The temperature of the stirred liquid medium was essentially constant. Three different levels of "flow" were simulated by varying the settings (2, 1 and 0) of an electromagnetic stirrer. The results qualitatively demonstrate that the invention is sensitive to changes in stirring rate of "flow" changes and repeatible within the hysteresis of the flow setting system.

EXAMPLE II

FIG. 7 shows the sensitivity of one embodiment of the present non-invasive invention (FIG. 1) using back-to-back thermistor flakes in thermal communication with a thermally regulated isolated perfused rat liver system designed to provide a wide range of calibrated (i.e., known) tissue perfusions.

The non-invasive probe consisted of two thermistor flakes mounted back-to-back and separated by a thin dielectric film. One flake serves as a thermal guard while the other "surface" flake is in thermal contact with the tissue medium. The probe (both flakes) is operated in two modes: sensing and heating. In the sensing mode the baseline temperature of the tissue is calculated from the resistance of the surface flake. In the heating mode, power is supplied separately to each flake so that the temperature of each flake is raised to a predetermined value. If the two flakes are heated to exactly the same temperature there is no net heat flux across the intervening dielectric and all of the heat that leaves the surface thermistor enters the abutting medium. Thus, when the probe is placed in contact with a medium, the power requirement of the surface thermistor is indicative of the thermal properties of that medium; that is, the more thermally conductive the medium, the greater the power required to maintain the surface flake at its elevated temperature.

After the non-invasive probe has been heated for a period of time (25 seconds), the thermistor power requirement is temporally identical to the power requirements of a spherical invasive probe. The thermal wavefront that propagates away from the probe as a result of heating the thermistors is initially planar; however, with increasing time (i.e., approximately 25 seconds), a spherical wavefront evolves. Thus at times greater than approximately 25 seconds a spherical model is applicable to the non-invasive probe and data collection and reduction protocols similar to those used for the invasive probe are also applicable. In particular, equations 5 and 7 were shown valid for the non-invasive work. A finite difference analysis confirmed the spherical wavefront at larger times.

$$P(t) = \Gamma + \beta f(t) \quad \text{Equation 5}$$

$$K_{eff} = (3\Delta T/\Gamma a_p - 0.2/K_p)^{-1} \quad \text{Equation 6}$$

$$W = (K_{eff} - K_m)^2 / K_m C_b l a_p^2 \quad \text{Equation 7}$$

where P(t)=applied power density required to establish and maintain temperature increment $\Delta T$ in watts/cm$^3$ $\Gamma$=steady state power density required to maintain temperature step, $\Delta T$. in watts/cm$^3$ $\beta$=slope of P(t) vs f(t) relationship from which thermal diffusivity $\alpha$ is derived.

$k_{eff}$=effective thermal conductivity (watt/cm° C.) which includes thermal effect of perfusion. In absence of perfusion $K_{eff}$ is equal to $K_m$.

$K_m$=intrinsic thermal conductivity (watt/cm° C.)

$\Delta T$=applied temperature increment, C, $a_p$ = characteristic probe dimension found via calibration in materials of known thermal properties, cm, $K_p$ = thermal conductivity of the probe (watt/cm° C.)

W = perfusion (ml of blood 100 gram tissue - min) or alternatively gm/ml-sec., and $C_{bl}$ = heat capacity of blood (watt-sec/gm° C.).

The resistance versus temperature calibration is carried out in a well-stirred water bath generally between 15° C. and 45° C. the resistance versus temperature curve is well fit by the following equation:

$(T = 27.3.15° C.)^{-1} = H_0 = H_1 \ln(R) + H_3 (\ln R)^3$

Probe conductivity, $K_p$, and characteristic dimension, $a_p$, were determined using equation 6 and two media of known thermal conductivity (water and glycerin).

Given $K_p$ and $a_p$, the ability to quantify accurately the thermal conductivity of media using the non-invasive probe was assessed using several media of known thermal conductivity. These media included several mixtures of water/agar and glycerin as well as solutions of pure water/agar and pure glycerin. The thermal conductivity of the mixtures was calculated from the mass fraction of its constituent ingredients.

The measurement procedure includes: (1) placing the probe on the surface of the medium, (2) monitoring the baseline temperature of the medium, (3) heating the thermistors to the desired ΔT and monitoring the power required to maintain that temperature step, (4) determining the steady-state power requirement of each thermistor and (5) calculating $K_m$ using Equation 6. The thermal conductivity of a medium could be determined within 2% error (see FIG. 6).

The ability of quantify perfusion must be treated against a standard. Such a standard exists in the form of the rat liver perfusion apparatus. Within this apparatus, temperature is controlled to within 0.005° C., 100% humidity is maintained, and surgically isolated rat liver is kept viable by perfusing it, via the portal vein, with oxygenated glucose Ringer's solution. The rate of perfusion can be controlled with a pinch valve and measured by collecting venous outflow. Using radiolabeled microspheres, perfusion can be quantified to within at most 8% error and the shunt fraction (typically less than 1% of the total flow) can be assessed. Measurements taken with the noninvasive thermistor probe were as outlined in steps 1-5 above. Note that Equation 6 is used to calculate $K_{eff}$ (perfusion W=0) and Equation 7 is used to calculate perfusion, w.

In the measurement of perfusion, it was found that determination of the intrinsic conductivity $K_m$ (non-flow value of conductivity) was a major source of error. However, given accurate intrinsic thermal conductivity, $K_m$, and calibration co-efficients, $K_p$ and $a_p$, perfusion can be quantified accurately within 4-5 mm of the surface (see FIG. 7). In this particular embodiment, both the surface thermistor and the backside guarding thermistor were sensitive to perfusion.

Tests with media of known thermal conductivity demonstrated that the thermal conductivity of a medium could be non-invasively quantified to within 2% error. The rat liver perfusion experiments demonstrate that the non-invasive probe was quite sensitive to changes in perfusion. A surprising result was that both the surface and guarding thermistors were sensitive to the thermal properties and perfusion in the abutting medium. This result is explained by observing heat the guarding thermistor heats the supporting substrate to which it was attached which, in turn, heats the abutting tissue. Thus, the heated substrate near the guarding flake contributes to its effective heating surface. This hypothesis is supported by observing that the calibrated characteristic dimension, $a_p$, for the guarding thermistor is greater than that for the surface thermistor, although each is of the same physical size.

The two flake thermistor non-invasive probe can accurately quantify the temperature and thermal conductivity of the medium upon which the probe is placed. Further, given accurate calibration coefficients, $K_p$ and $a_p$, and the intrinsic thermal conductivity of the tissue medium, $K_m$, the probe can accurately quantify (within approximately 15% error) perfusion within the 4-5 mm surface regions of the tissue.

We claim:

1. Apparatus for measuring thermal conductivity, thermal diffusivity and/or fluid perfusion within a biomaterial in a nonsteady state non-invasively comprising:
   a. a non-invasive first heat transfer and temperature sensing means positioned in direct thermal communication with said biomaterial,
   b. a non-invasive second heat transfer and temperature sensing means positioned in thermal communication with said first heat transfer and temperature sensing means,
   c. non-invasive means for changing the temperature of said first heat transfer and temperature sensing means.
   d. non-invasive means for changing the temperature of said second heat transfer and temperature sensing means so as to substantially prevent net heat flow between said first heat transfer and temperature sensing means and said second heat transfer and temperature sensing means
   e. non-invasive means for quantifying the heat flow between said first heat transfer and temperature sensing means to a surface of said biomaterial, and
   f. means for determining thermal conductivity, thermal diffusivity and/or perfusion as a function of time dependent heat dissipation during a period of fixed temperature elevation or measured rate of change of temperature of said first heat transfer and temperature sensing means, by determining a rate of heat transfer between said first heat trasnfer and temperature sensing means and said biomaterial in a coupled fashion in conjunction with boundary and initial conditions,
   said apparatus having a size and thermal conductivity such that the thermal responsive time of said apparatus between a time of measuring temperature of said first heat transfer and temperature sensing means and a time power is supplied to said first heat transfer and temperature sensing means being less than five seconds.

2. The apparatus of claim 1 wherein said means for changing temperature of said second heat transfer and temperature sensing means substantially prevents net heat flow between said first heat transfer and temperature sensing means and said second heat transfer and temperature sensing means.

3. The apparatus of any one of claims 1 or 2 wherein said first and second heat transfer and temperature sensing means are thermistors.

4. The apparatus of any one of claims 1 or 2 wherein a third heat transfer and temperature sensing means is in thermal communication with said first heat transfer and temperature sensing means.

5. The process for non-invasively measuring thermal conductivity, thermal diffusivity and/or fluid perfusion within a surface layer of a biomaterial in a nonsteady state which comprises contacting the first heat transfer and temperature sensing means of the apparatus of claim 1 to the surface of the biomaterial, introducing power into the second heat transfer and temperature sensing means of the apparatus of claim 1, quantifying heat flow into said biomaterial without invading said biomaterial with said first heat transfer and temperature sensing means and said second heat transfer and temperature sensing means and determining thermal conductivity, thermal diffusivity and/or perfusion as time dependent heat dissipation during the period of fixed temperature elevation or measured time rate of change of temperature of said first heat transfer and temperature sensing means by determining the rate of heat transfer between said first heat transfer and temperature sensing means and said biomaterial in a coupled fashion in conjugation with boundary and initial conditions.

6. The process of claim 5 wherein said heat flow from said heat source and second heat transfer and temperature sensing means is insulated by heating at least one surface of said heat source not in contact with said surface layer, thereby to render said at least one surface adiabatic.

7. The apparatus of claim 1 where said means for changing the temperature of said second heat transfer and temperature means quantifies said net heat flow between said first and second heat transfer and temperature sensing means.

8. Apparatus for measuring thermal conductivity, thermal diffusivity and/or fluid perfusion within a biomaterial in a non-steady state non-invasively comprising:
   a. a noninvasive first heat transfer and temperature sensing means,
   b. a noninvasive second heat transfer and temperature sensing means positioned in thermal communication with said first heat transfer and temperature sensing means,
   c. noninvasive means for changing the temperature of said first heat transfer and temperature sensing means,
   d. noninvasive means to quantify said net heat flow between said first and second heat transfer and temperature sensing means, and
   e. noninvasive means for quantifying the heat flow between said first heat transfer and temperature sensing means to a surface of said biomaterial, and
   f. means for determining thermal conductivity, thermal diffusivity and/or perfusion as a function of time dependent heat dissipation during a period of fixed temperature elevation or measured time rate of change of temperature of said first heat transfer and temperature sensing means by determining a rate of heat transfer between said first heat transfer and temperature sensing means and said biomaterial in a coupled fashion in conjugation with boundary and initial conditions, said apparatus having a size and thermal conductivity such that the thermal responsive time of said apparatus between a time of measuring temperature of said first heat transfer and temperature sensing means and a time power is supplied to said first heat transfer and temperature sensing means being less than five seconds.

9. The apparatus of claim 8 wherein said means for changing temperature of said second heat transfer and temperature sensing means substantially prevents net heat flow between said first heat transfer and temperature sensing means and said second heat transfer and temperature sensing means.

10. The apparatus of any one of claims 8 or 9 wherein said first and second heat transfer and temperature sensing means are thermistors.

11. The apparatus of any of of claims 8 or 9 wherein a third heat transfer and temperature sensing means is in thermal communication with said first heat transfer and temperature sensing means.

12. The process for non-invasively measuring the thermal conductivity, thermal diffusivity and/or fluid perfusion within a surface layer of a biomaterial in a non-steady state which comprises contacting the first heat transfer and temperature sensing means of the apparatus of claim 8 to the surface of the biomaterial, introducing power into the second heat trasnfer and temperature sensing means of the apparatus of claim 8, quantifying heat flow into said biomaterial without invading said biomaterial with said first heat transfer and temperature sensing means and said second head transfer and temperature sensing means and determining thermal conductivity, thermal diffusivity and/or perfusion as a function of time dependent heat dissipation during the period of fixed temperature elevation or measured flow between said first and second heat transfer and temperature sensing means by determining the rate of heat transfer between said first heat transfer and temperature sensing means and said biomaterial in a coupled fashion in conjugation with boundary and initial conditions.

13. The process of claim 12 wherein said heat flow from said second heat transfer and temperature sensing means is insulated by heating at least one surface of said heat source not in contact with said surface layer, thereby to render said at least one surface adiabatic.

14. The process of any one of claims 12 or 13 wherein the heat quantified is related to fluid perfusion within said medium.

15. The process of any one of claims 12 or 13 wherein the heat quantified is related to blood perfusion within said biomaterial.

* * * * *